United States Patent [19]
Schlaefer et al.

[11] Patent Number: 5,856,611
[45] Date of Patent: Jan. 5, 1999

[54] ZIRCONIUM CATALYZED TRANSESTERIFICATION PROCESS FOR PREPARING SYNTHETIC WAX MONOMERS

[75] Inventors: Francis William Schlaefer, Penllyn; Andrew William Gross, Hatboro, both of Pa.

[73] Assignee: Rohm and Haas Company, Philadelphia, Pa.

Related U.S. Application Data

[60] Provisional application No. 60/028,885 Oct. 17, 1996.

[21] Appl. No.: 950,443
[22] Filed: Oct. 15, 1997
[51] Int. Cl.$^6$ ............................. C07C 2/02; C07C 2/50; C07C 51/43
[52] U.S. Cl. ......................... 585/520; 585/523; 585/709; 554/1; 554/174
[58] Field of Search ...................... 585/520, 523, 585/704; 554/1, 174

[56] References Cited

U.S. PATENT DOCUMENTS 5,037,978   8/1991   Mirabelli ................................ 544/171

FOREIGN PATENT DOCUMENTS

| 2602229 A1 | 2/1988 | France . |
| 2805702 | 2/1978 | Germany . |
| 6-329720 | 11/1994 | Japan . |

*Primary Examiner*—Nathan M. Nutter
*Attorney, Agent, or Firm*—Kevin F. Gironda; John L. Lemanowicz

[57] ABSTRACT

A zirconium catalyzed transesterification process for preparing synthetic wax monomers is disclosed. The monomers are useful in a wide range of polymers.

5 Claims, No Drawings

ZIRCONIUM CATALYZED TRANSESTERIFICATION PROCESS FOR PREPARING SYNTHETIC WAX MONOMERS

This is a nonprovisional application of prior pending provisional application Ser. No. 60/028,885 filed Oct. 17, 1996.

This invention relates to a process for preparing monomers, in particular to a process suitable for preparing monomers useful in a wide range of polymers.

High molecular weight ($C_{20}$–$C_{300}$) alcohols are known as synthetic wax alcohols, and have been in commercial production for several years. Whereas synthetic wax alcohols have limited use in candle wax, synthetic wax monomers are quite useful in a wide range of polymers. The use of synthetic wax alcohols would increase significantly if there was a process to convert them into synthetic wax monomers. There is an ongoing need for a process for preparing synthetic wax monomers from synthetic wax alcohols.

Japanese Patent Application J 6-329720 discloses polyethylene macromonomers with a (meth)acryloyl terminal group and a method for preparation of these monomers. According to the disclosed method, a polyethylene derivative is reacted with specific carbonyl compounds, or is oxidized with oxygen to produce polyethylene alkoxide, and subsequently reacted with (meth)acrylic acid halide to yield the desired product.

Another method known in the art is the use of transesterification to produce short chain acrylate esters. This method has routinely been performed utilizing catalysts selected from Group IVA elements such as, for example Sn, Ge, and Pb; Group IVB elements such as, for example, Ti and Hf; Group VA elements such as, for example, As and Sb; and Group VIII element Fe, see for example U.S. Pat. No. 5,037,948. These catalysts require relatively high use levels to be effective, and can be difficult to remove from the final product.

Strong acids such as, for example, methane sulfonic acid and strong alkalies such as, for example, lithium hydroxide are also known to catalyze transesterifications. These catalysts also are undesirable because of their corrosive nature. If not removed from the product, these catalysts may interfere with subsequent polymerizations and end uses. Removal of the catalyst from the product is also difficult.

Despite the disclosure of the prior art, there is a continuing need for a process for preparing synthetic wax monomers from synthetic wax alcohols.

We have surprisingly found that zirconium compounds are extremely effective at catalyzing the transesterification reactions which produce synthetic wax monomers from synthetic wax alcohols. Very low levels of zirconium compounds can be used effectively. An advantage of the present invention is that the zirconium compound does not need to be removed from the final product, due to its low usage level and benign character in downstream applications.

The present invention provides a process for preparing synthetic wax monomers comprising:
admixing a synthetic wax alcohol, a (meth)acrylate ester, a zirconium compound, and an inhibitor selected from the group consisting of nitroxyl radical containing compounds, hydroquinone, methoxy hydroquinone, phenothiazine, and copper compounds;
heating the mixture to 100° C.–165° C. to provide the synthetic wax monomer; and removing the lower alcohol from the synthetic wax alcohol and the (meth) acrylate ester.

The lower alcohol formed from reaction of the synthetic wax alcohol and the (meth)acrylate ester may be removed by fractional distillation. The excess (meth)acrylate ester may be stripped from the product.

Synthetic wax alcohols are commercially available as Unilin ™ or Unithox™ products sold through Petrolite Inc. Suitable synthetic wax alcohols for use in this invention include ($C_{20}$–$C_{50}$) linear alcohols and ethoxylates thereof (Meth)acrylate esters are commercially available from Rohm and Haas Company. Suitable (meth)acrylate esters for use in this invention include but are not limited to methyl acrylate, ethyl acrylate, propyl acrylate, and n-butyl acrylate; and methyl methacrylate, ethyl methacrylate, propyl methacrylate, n-butyl methacrylate, isopropyl methacrylate, isobutyl methacrylate, and t-butyl methacrylate.

Typically, the (meth)acrylate ester and synthetic wax alcohol are reacted on a molar basis of from 2 (meth)acrylate ester to 1 synthetic wax alcohol to 10 (meth)acrylate ester to 1 synthetic wax alcohol. More preferred is a ratio of from 3 (meth)acrylate ester to 1 synthetic wax alcohol to 9 (meth) acrylate ester to 1 synthetic wax alcohol. Most preferred is a ratio of from 4 (meth)acrylate ester to 1 synthetic wax alcohol to 8 (meth)acrylate ester to 1 synthetic wax alcohol.

Zirconium compounds are commercially available through Aldrich Chemical Company. Suitable zirconium compounds for use in this invention include zirconium acetylacetonate, zirconium butoxide, zirconium tert-butoxide, zirconium chloride, zirconium citrate ammonium complex, zirconium ethoxide, zirconium fluoride, zirconium hydride, zirconium isopropoxide isopropanol complex, zirconium oxide, zirconium propoxide, zirconium sulfate hydrate, zirconium tetrachloride, and zirconium silicate. Zirconium acetylacetonate is preferred. The zirconium compound may be added at from 0.1% to 10% based on the moles of synthetic wax alcohol. More preferred is from 0.5% to 7.5% zirconium compound based on the moles of synthetic wax alcohol. Most preferred is from 1% to 4% zirconium compound based on the moles of synthetic wax alcohol.

Suitable inhibitors for use in this invention include, but are not limited to nitroxyl radical containing compounds, hydroquinone, methoxy hydroquinone, phenothiazine, and copper compounds. The inhibitors are commercially available through Aldrich Chemical Company. Suitable copper compounds include cupric acetate, cupric bromide, cupric chloride, cupric 2-ethylhexanoate, cupric fluoride, cupric gluconate, cupric nitrate, cupric methoxide, cupric sulfate, and cupric dibutyl dithio carbamate. Cupric dibutyl dithio carbamate is preferred. Suitable nitroxyl radical containing compounds include 2,2,6,6-tetramethyl-1-piperidinyloxy, free radical ("4-hydroxy-TEMPO"), 4-oxo-2,2,6,6-tetramethyl-1-piperidinyloxy, free radical ("4-oxo-TEMPO"), and di-tertiary butyl nitroxyl (DtBN)(available through Nova Molecular Technologies, Lake Geneva, Wis.). The inhibitor may be added at from 100 ppm to 4,000 ppm based on the total weight of the synthetic wax alcohol and (meth)acrylate ester to be reacted. More preferred is from 500 ppm to 3,000 ppm inhibitor based on the total weight of the synthetic wax alcohol and (meth)acrylate ester to be reacted. Most preferred is from 1,000 ppm to 2,000 ppm inhibitor based on the total weight of the synthetic wax alcohol and (meth)acrylate ester to be reacted.

The following examples are intended to illustrate the process for making synthetic wax monomers from synthetic wax alcohols. All percentages are on a weight basis. Abbreviations used are: g=grams, mm=millimeters, l=liter, %=percent, $N_2$=nitrogen, $O_2$=oxygen, n=normal, and °C.=degrees Centigrade.

EXAMPLE 1

Acrylate of $C_{40}$ Alcohol

A 5 l flask equipped with an overhead stirrer, a 10 plate-2 inch Oldershaw column, a thermocouple and controller, a graduated receiver, a magnetically controlled reflux head, and an 8% $O_2$/92% $N_2$ sparge at 19.5 cubic centimeters per minute was charged with 2,000 g of Unilin™ 550 (a primary, linear synthetic wax alcohol). To this was added 1,164 g n-butyl acrylate and 1.4 g 4-hydroxy-TEMPO. While agitating and sparging, the batch was heated to 100° C. When a homogenous solution was obtained, 20.0 g zirconium acetylacetonate was added. The vacuum was increased to 200 mm and the temperature was increased to 120° C.–125° C. The vacuum and temperature were held constant until the vapor temperature reached 97° C. At this point, transesterification was complete. The total time from zirconium acetyl acetonate addition to completion of the reaction was 2.45 hours. The vacuum and temperature were lowered. The column was removed and a straight-lead take-off head was installed. The vacuum was then increased to 25 mm and the temperature was increased to 125° C. The temperature and vacuum were held until distillation stopped. The molten product was dropped out at 125° C. Conversion of the Unilin™ 550 alcohol to the acrylate ester was quantitative as measured by Nuclear Magnetic Resonance ("NMR"). The product contained 0.12% residual butyl acrylate as measured by Gas Chromatography ("GC").

EXAMPLE 2

Acrylate Of $C_{50}$ Alcohol

A 5 l flask equipped with an overhead stirrer, a 10 plate-2 inch Oldershaw column, a thermocouple and controller, a graduated receiver, a magnetically controlled reflux head, and an 8% $O_2$/92% $N_2$ sparge at 19.5 cubic centimeters per minute was charged with 2,500 g of Unilin™ 700 (a primary, linear synthetic wax alcohol). To this was added 1,250 g n-butyl acrylate and 1.75 g 4-hydroxy-TEMPO. While agitating and sparging, the batch was heated to 100° C. When a homogenous solution was obtained, 25.0 g zirconium acetylacetonate was added. The vacuum was increased to 200 mm and the temperature was increased to 120° C.–125° C. The vacuum and temperature were held constant until the vapor temperature reached 97° C. At this point, transesterification was complete. The total time from zirconium acetyl acetonate addition to completion of the reaction was 2.37 hours. The vacuum and temperature were lowered. The column was removed and a straight-lead take-off head was installed. The vacuum was then increased to 25 mm and the temperature was increased to 125° C. The temperature and vacuum were held until distillation stopped. The molten product was dropped out at 125° C. Conversion of the Unilin™ 700 alcohol to the acrylate ester was 98.5% as measured by NMR. The product contained 0.1% residual butyl acrylate as measured by GC.

EXAMPLE 3

Acrylate Of $C_{22}$ Alcohol

A 5 l flask equipped with an overhead stirrer, a 10 plate-2 inch Oldershaw column, a thermocouple and controller, a graduated receiver, a magnetically controlled reflux head, and an 8% $O_2$/92% $N_2$ sparge at 19.5 cubic centimeters per minute was charged with 456.4 g of Nafol™ 1822 Alcohol (a primary, linear synthetic wax alcohol/100% functionality). To this was added 581.5 g n-butyl acrylate and 0.7 g 4-hydroxy-TEMPO. While agitating and sparging, the batch was heated to 100° C. When a homogenous solution was obtained, 9.9 g zirconium acetylacetonate was added. The vacuum was increased to 200 mm and the temperature was increased to 120° C.–125° C. The vacuum and temperature were held constant until the vapor temperature reached 97° C. At this point, transesterification was complete. The total time from zirconium acetyl acetonate addition to completion of the reaction was 0.90 hours. The vacuum and temperature were lowered. The column was removed and a straight-lead take-off head was installed. The vacuum was then increased to 25 mm and the temperature was increased to 125° C. The temperature and vacuum were held until distillation stopped. The molten product was dropped out at 125° C. Conversion of the Nafol™ 1822 Alcohol to the acrylate ester was quantitative as measured by NMR. The product contained 0.24% residual butyl acrylate and 0.08% residual butanol as measured by GC.

EXAMPLE 4

Acrylate Of Ethoxylated Alcohol

A 5 l flask equipped with an overhead stirrer, a 10 plate-2 inch Oldershaw column, a thermocouple and controller, a graduated receiver, a magnetically controlled reflux head, and an 8% $O_2$/92% $N_2$ sparge at 19.5 cubic centimeters per minute was charged with 2,373.5 g of Unithox™ 450 Ethoxylate (an ethoxylated primary, linear synthetic wax alcohol/82% alcohol functionality). To this was added 809.6 g n-butyl acrylate and 1.2 g 4-hydroxy-TEMPO. While agitating and sparging, the batch was heated to 100° C. When a homogenous solution was obtained, 20.0 g zirconium acetylacetonate was added. The vacuum was increased to 200 mm and the temperature was increased to 165° C. The vacuum and temperature were held constant until the vapor temperature reached 97° C. At this point, transesterification was complete. The total time from zirconium acetyl acetonate addition to completion of the reaction was 3.60 hours. The vacuum and temperature were lowered. The column was removed and a straight-lead take-off head was installed. The vacuum was then increased to 25 mm and the temperature was increased to 125° C. The temperature and vacuum were held until distillation stopped. The molten product was dropped out at 125° C. Conversion of the Unithox™ 450 Ethoxylate Alcohol to the acrylate ester was 92% as measured by NMR. The product contained 0.04% residual butyl acrylate as measured by GC.

EXAMPLE 5

Methacrylate Of $C_{33}$ Alcohol

A 5 l flask equipped with an overhead stirrer, a 10 plate-2 inch Oldershaw column, a thermocouple and controller, a graduated receiver, a magnetically controlled reflux head, and an 8% $O_2$/92% $N_2$ sparge at 19.5 cubic centimeters per minute was charged with 430 g of Unilin 425™ (a primary, linear synthetic wax alcohol/84.3% alcohol functionality). To this was added 240.3 g methyl methacrylate and 0.5 g 4-hydroxy-TEMPO. While agitating and sparging, the batch was heated to 100° C. When a homogenous solution was obtained, 2.5 g zirconium acetylacetonate was added. The vacuum was increased to 400 mm and the temperature was increased to 135° C. The vacuum and temperature were held constant until the vapor temperature reached 97° C. At this point, transesterification was complete. The total time from zirconium acetyl acetonate addition to completion of the reaction was 1.0 hours. The vacuum and temperature were lowered. The column was removed and a straight-lead take-off head was installed. The vacuum was then increased to 25 mm and the temperature was increased to 125° C. The temperature and vacuum were held until distillation stopped. The molten product was dropped out at 125° C. Conversion of the Unilin™ 425 alcohol to the acrylate ester was quantitative as measured by NMR. No residual methyl methacrylate was detected as measured by GC.

EXAMPLE 6

Acrylate Of C40 Alcohol And Comparison Of Inhibitors

Example 1 was repeated and 1,4-hydroquinone was substituted for 4-hydroxy-TEMPO. A 5 l flask equipped with an overhead stirrer, a 10 plate-2 inch Oldershaw column, a thermocouple and controller, a graduated receiver, a magnetically controlled reflux head, and an 8% $O_2$/92% $N_2$ sparge at 19.5 cubic centimeters per minute was charged with 2,000 g of Unilin™ 550 (a primary, linear synthetic wax alcohol). To this was added 1,164 g n-butyl acrylate and 1.4 g 1,4-hydroquinone. While agitating and sparging, the batch was heated to 100° C. When a homogenous solution was obtained, 20.0 g zirconium acetylacetonate was added. The vacuum was increased to 200 mm and the temperature was increased to 120° C.–125° C. The vacuum and temperature were held constant until the vapor temperature reached 97° C. At this point, transesterification was complete. The total time from zirconium acetyl acetonate addition to completion of the reaction was 2.45 hours. The vacuum and temperature were lowered. The column was removed and a straight-lead take-off head was installed. The vacuum was then increased to 25 mm and the temperature was increased to 125° C. The temperature and vacuum were held until distillation stopped. The molten product was dropped out at 125° C. Conversion of the Unilin™ 550 alcohol to the acrylate ester was greater than 98% as measured by NMR. The product contained 0.28% residual butyl acrylate as measured by GC.

EXAMPLE 7

Methacrylate Of $C_{40}$ Alcohol With Hydroquinone Inhibitor

A 5 l flask equipped with an overhead stirrer, a 10 plate-2 inch Oldershaw column, a thermocouple and controller, a graduated receiver, a magnetically controlled reflux head, and an 8% $O_2$/92% N2 sparge at 19.5 cubic centimeters per minute was charged with 500 g of Unilin™ 550 (a primary, linear synthetic wax alcohol). To this was added 375 g methyl methacrylate and 0.4 g hydroquinone. While agitating and sparging, the batch was heated to 110° C. When a homogenous solution was obtained, 0.8 g zirconium acetylacetonate was added. The reaction was distilled at this temperature for 3 hours. Another 0.4 g zirconium acetylacetonate was added, the pot temperature was raised to 125° C., and the reaction was distilled for an hour. The total time from zirconium acetyl acetonate addition to completion of the reaction was 4.15 hours. The column was removed and a straight-lead take-off head was installed. The vacuum was then increased to 25 mm and the temperature was increased to 1250° C. The temperature and vacuum were held until distillation stopped. The molten product was dropped out at 1250° C. Conversion of the Unilin™ 550 alcohol to the methacrylate ester was quantitative as measured by NMR. The product contained 0.45% residual methyl methacrylate as measured by GC.

EXAMPLE 8

Methacrylate Of Ethoxvlated Alcohol With Hydroquinone Inhibitor

A 5 l flask equipped with an overhead stirrer, a 10 plate-2 inch Oldershaw column, a thermocouple and controller, a graduated receiver, a magnetically controlled reflux head, and an 8% $O_2$/92% $N_2$ sparge at 19.5 cubic centimeters per minute was charged with 451 g of Unithox™ 450 (an ethoxylated primary, linear synthetic wax alcohol/82% functionality). To this was added 719 g methyl methacrylate and 1.0 g hydroquinone. While agitating and sparging, the batch was heated to 100° C. When a homogenous solution was obtained, 3.77 g zirconium acetylacetonate was added. The vacuum was increased to 200 mm and the temperature was increased to 1080° C. The reaction was distilled for 2.5 hours. The total time from zirconium acetyl acetonate addition to completion of the reaction was 3.0 hours. The vacuum and temperature were lowered. The column was removed and a straight-lead take-off head was installed. The residual methyl methacrylate was stripped for another 1 hour. The molten product was dropped out at 108° C. Conversion of the Unithox™ 450 alcohol to the methacrylate ester was 92% as measured by NMR. The product contained 0.44% residual methyl methacrylate as measured by GC.

EXAMPLE 9—COMPARATIVE EXAMPLE

Acrylate Of $C_{40}$ Alcohol With Potassium tert-Butoxide

A 5 l flask equipped with an overhead stirrer, a 10 plate-2 inch Oldershaw column, a thermocouple and controller, a graduated receiver, a magnetically controlled reflux head, and an 8% $O_2$1 92% N2 sparge at 19.5 cubic centimeters per minute was charged with 2,000 g of Unilin™ 550 (a primary, linear synthetic wax alcohol). To this was added 1,164 g n-butyl acrylate and 1.4 g 4-hydroxy-TEMPO. While agitating and sparging, the batch was heated to 100° C. When a homogenous solution was obtained, 20.0 g potassium tert-butoxide was added. The vacuum was increased to 200 mm and the temperature was increased to 120° C.–125° C. The vacuum and temperature were held constant until the vapor temperature reached 97° C. The total time from zirconium acetyl acetonate addition to completion of the reaction was 2.45 hours. The vacuum and temperature were lowered. The column was removed and a straight-lead take-off head was installed. The vacuum was then increased to 25 mm and the temperature was increased to 125° C. The temperature and vacuum were held until distillation stopped. The molten product was dropped out at 125° C. Conversion of the Unilin™ 550 alcohol to the acrylate ester was 10.7% as measured by NMR. The product contained 0.63% residual butyl acrylate as measured by GC.

EXAMPLE 10—COMPARATIVE EXAMPLE

Acrylate Of $C_{40}$ Alcohol With Dibutyltin Methoxide

A 5 l flask equipped with an overhead stirrer, a 10 plate-2 inch Oldershaw column, a thermocouple and controller, a graduated receiver, a magnetically controlled reflux head, and an 8% $O_2$/92% $N_2$ sparge at 19.5 cubic centimeters per minute was charged with 2,000 g of Unilin™ 550 (a primary, linear synthetic wax alcohol). To this was added 1,164 g n-butyl acrylate and 1.4 g 4-hydroxy-TEMPO. While agitating and sparging, the batch was heated to 100° C. When a homogenous solution was obtained, 20.0 g dibutyltin dimethoxide was added. The vacuum was increased to 200 mm and the temperature was increased to 120° C.–125° C. The vacuum and temperature were held constant until the vapor temperature reached 97° C. At this point, transesterification was complete. The total time from zirconium acetyl acetonate addition to completion of the reaction was 2.45 hours. The vacuum and temperature were lowered. The column was removed and a straight-lead take-off head was installed. The vacuum was then increased to 25 mm and the temperature was increased to 125° C. The temperature and vacuum were held until distillation stopped. The molten product was dropped out at 125° C. Conversion of the Unilin™ 550 alcohol to the acrylate ester was quantitative as measured by NMR. The product contained 0.64% residual butyl acrylate as measured by GC. Although the conversion was good, tin is quite toxic and has to be removed from the product. Removal of tin from the product is very difficult.

EXAMPLE 11—COMPARATIVE EXAMPLE

Acrylate Of $C_{40}$ Alcohol With Magnesium Methoxide

A 5 l flask equipped with an overhead stirrer, a 10 plate-2 inch Oldershaw column, a thermocouple and controller, a graduated receiver, a magnetically controlled reflux head, and an 8% $O_2$/92% $N_2$ sparge at 19.5 cubic centimeters per minute was charged with 2,000 g of Unilin™ 550 (a primary, linear synthetic wax alcohol). To this was added 1,164 g n-butyl acrylate and 1.4 g 4-hydroxy-TEMPO. While agitating and sparging, the batch was heated to 100° C. When a homogenous solution was obtained, 20.0 g magnesium methyl carbonate (8% in methanol) was added. The vacuum was increased to 200 mm and the temperature was increased to 120° C.–125° C. The vacuum and temperature were held constant until the vapor temperature reached 97° C. The total time from zirconium acetyl acetonate addition to completion of the reaction was 2.45 hours. The vacuum and temperature were lowered. The column was removed and a straight-lead take-off head was installed. The vacuum was then increased to 25 mm and the temperature was increased to 125° C. The temperature and vacuum were held until distillation stopped. The molten product was dropped out at 125° C. Conversion of the Unilin™ 550 alcohol to the acrylate ester was 1.5% as measured by NMR. The product contained 0.8% residual butyl acrylate as measured by GC.

The above examples demonstrate that the process of this invention is very effective at converting synthetic wax alcohols into synthetic wax monomers without the need for removing the catalyst from the product. The other catalysts tested either gave poor conversion of the synthetic wax alcohol into the synthetic wax monomer, or require removal of the catalyst from the product.

What is claimed:

1. A process for preparing synthetic wax monomers comprising:

admixing a synthetic wax alcohol, a (meth)acrylate ester selected from the group consisting of methyl (meth) acrylate, ethyl (meth)acrylate, propyl (meth)acrylate, n-butyl (meth)acrylate, isopropyl methacrylate, isobutyl methacrylate, and t-butyl methacrylate, a zirconium compound selected from zirconium acetylacetonate, zirconium butoxide, zirconium tert-butoxide, zirconium chloride, zirconium citrate ammonium complex, zirconium ethoxide, zirconium fluoride, zirconium hydride, zirconium isopropoxide isopropanol complex, zirconium oxide, zirconium propoxide, zirconium sulfate hydrate, zirconium tetrachloride, and zirconium silicate, and an inhibitor selected from the group consisting of nitroxyl radical containing compounds, hydroquinone, methoxy hydroquinone, phenothiazine, and copper compounds selected from cupric acetate, cupric bromide, cupric chloride, cupric 2-ethylhexanoate, cupric fluoride, cupric gluconate, cupric nitrate, cupric methoxide, cupric sulfate, and cupric dibutyl dithio carbamate:

heating the mixture to 100° C.–165° C. to provide the synthetic wax monomer; and removing the lower alcohol from the synthetic wax alcohol and the (meth)acrylate ester.

2. The process according to claim 1 wherein the (meth) acrylate ester is methyl (meth)acrylate, the zirconium compound is zirconium acetylacetonate, and the inhibitor is 2,2,6,6-tetramethyl-1-piperidinyloxy, free radical.

3. The process according to claim 1 wherein the (meth) acrylate ester is n-butyl (meth)acrylate, the zirconium compound is zirconium acetylacetonate, and the inhibitor is 2,2,6,6-tetramethyl-1-piperidinyloxy, free radical.

4. The process according to claim 1 wherein the synthetic wax alcohol is selected from the group consisting of ($C_{20}$–$C_{50}$) linear alcohols and ethoxylates thereof.

5. The process according to claim 1 further comprising the additional step of stripping off the excess (meth)acrylate ester.

* * * * *